United States Patent [19]

Kato et al.

[11] Patent Number: 5,436,401
[45] Date of Patent: Jul. 25, 1995

[54] 22-OXACHOLECALCIFEROL DERIVATIVE AND PROCESS FOR PREPARING THE SAME

[75] Inventors: Masahiro Kato; Tetsuhiro Mikami; Kiyoshige Ochi, all of Tokyo; Hiroyoshi Watanabe; Noboru Kubodera, both of Shizuoka, all of Japan

[73] Assignee: Chugai Seiyaku Kabushiki Kaisha, Tokyo, Japan

[21] Appl. No.: 244,818

[22] PCT Filed: Dec. 18, 1992

[86] PCT No.: PCT/JP92/01662

§ 371 Date: Jun. 13, 1994

§ 102(e) Date: Jun. 13, 1994

[87] PCT Pub. No.: WO93/12083

PCT Pub. Date: Jun. 24, 1993

[30] Foreign Application Priority Data

Dec. 18, 1991 [JP] Japan ................... 3-361051

[51] Int. Cl.$^6$ ............... C07J 3/00; C07J 75/00
[52] U.S. Cl. ................... 552/610; 552/611; 568/665; 204/157.15; 204/157.67; 204/157.9; 204/157.92
[58] Field of Search ............ 204/157.65, 157.67, 204/157.9, 157.92; 568/665, 653, 610, 611

[56] References Cited

FOREIGN PATENT DOCUMENTS 61-140560 6/1986 Japan .
267550 11/1986 Japan .
61-267550 11/1986 Japan .
3188061 8/1991 Japan .

OTHER PUBLICATIONS

"Reactions of Carbonyl Compounds with Grignard Reagents in the Presence of Cerium Chlpride" Journal of the American Chemical Society, vol. III, No. 12, Jun. 7, 1989, 4392–4398.

*Primary Examiner*—John Niebling
*Assistant Examiner*—Edna Wong
*Attorney, Agent, or Firm*—Browdy and Neimark

[57] ABSTRACT

A 22-oxacholecalciferol derivative represented by formula (I):

wherein $R_1$ represents a hydrogen atom or a hydroxyl group; and $R_2$ and $R_3$, which may be the same or different, each represent a lower alkyl group having from 1 to 5 carbon atoms, and a process for preparing the same are disclosed. The compound of the present invention has potent differentiation inducing activity and cell proliferation inhibitory activity and is expected to be useful as an anti-tumor agent, an antirheumatic, a treating agent for psoriasis, and a treating agent for hyperparathyreosis. The process of the present invention makes it possible to efficiently produce a desired 22-oxacholecalciferol derivative while reducing by-production.

8 Claims, No Drawings

22-OXACHOLECALCIFEROL DERIVATIVE AND PROCESS FOR PREPARING THE SAME

FIELD OF THE INVENTION

This invention relates to a 22-oxacholecalciferol derivative expected useful as a drug, an intermediate for the same, and a process for preparing the 22-oxacholecalciferol derivative using the intermediate.

BACKGROUND OF THE INVENTION

22-Oxacholecalciferol derivatives have hitherto been prepared by, for example, the process starting with a compound represented by formula (II):

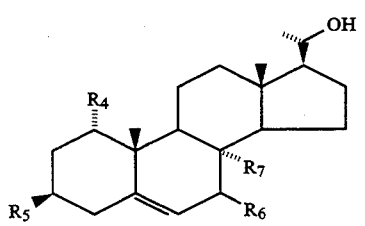

wherein $R_4$ represents a hydrogen atom, a hydroxyl group or a protected hydroxyl group; $R_5$ represents a hydroxyl group or a protected hydroxyl group; and $R_6$ and $R_7$ represent a hydrogen atom respectively or they are taken together to form a double bond, as disclosed in Japanese Patent Public Disclosure No. 267550/86. This process, as illustrated by the following reaction scheme (1), comprises reacting the compound of formula (II) with 1-bromo-3-propene in the presence of a basic catalyst to form a 20S-(3-butenyloxy) compound, oxidizing the 20S-(3-butenyloxy) compound with oxygen in the presence of a catalyst to obtain a 20S-(3-oxobutyloxy) compound, and reacting the 20S-(3-oxobutyloxy) compound with a Grignard reagent to obtain a 20S-(3-hydroxy-3-methylbutyloxy) compound.

[Reaction Scheme (1)]

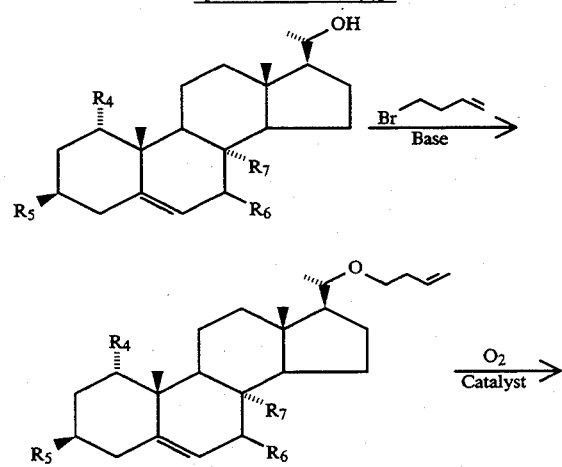

-continued
[Reaction Scheme (1)]

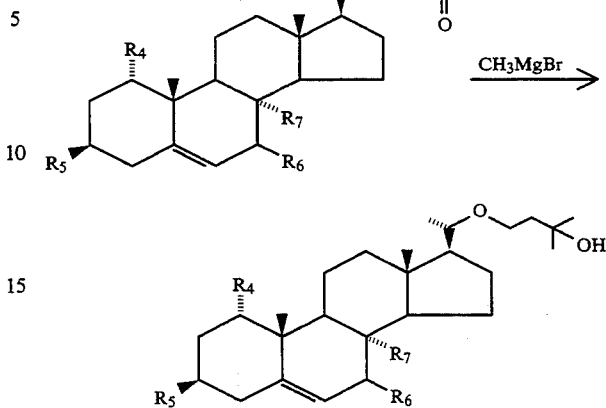

However, the above process requires complicated operation. In addition, since the reaction between the compound (II) and 1-bromo-3-propene is attended by by-production of a 20S-(2-butenyloxy) compound in a considerable proportion, resulting in a low yield of the desired compound, and separation and purification of the desired compound involves difficulty.

DISCLOSURE OF THE INVENTION

As a result of extensive investigations, the inventors have found a technique for constructing the side chain by O-alkylating the 20-hydroxyl group with a compound represented by formula (III):

$$CH_2=CH-COR_8 \qquad (III)$$

wherein $R_8$ represents a dialkylamino group having from 1 to 5 carbon atoms, and reached the present invention based on this finding. The process of the present invention starts from a compound represented by formula (II):

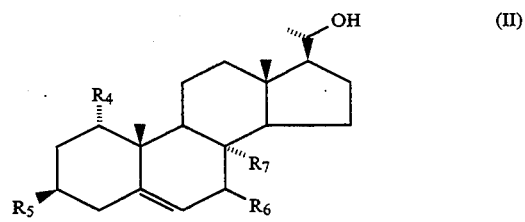

wherein $R_4$ represents a hydrogen atom, a hydroxyl group or a protected hydroxyl group; $R_5$ represents a hydroxyl group or a protected hydroxyl group; and $R_6$ and $R_7$ represent a hydrogen atom respectively or they are taken together to form a double bond.

The compound of formula (II) can be synthesized by, for example, the process disclosed in Japanese Patent Public Disclosure No. 267550/86.

Where starting with the compound of formula (II) in which the hydroxyl group(s) are protected, the protecting groups for a hydroxyl group include those which are not released under a basic condition, such as lower alkylsilyl groups, e.g., a trimethylsilyl group, a triethylsilyl group, and a t-butyldimethylsilyl group, with a t-butyldimethylsilyl group being preferred.

The compound of formula (II) is reacted with a compound represented by formula (III):

$$CH_2=CH-COR_8 \quad (III)$$

wherein $R_8$ represents a dialkylamino group having from 1 to 5 carbon atoms, in the presence of a basic catalyst.

Examples of the compound of formula (III) include acrylamide compounds, such as dimethylacrylamide and diethylacrylamide.

Examples of suitable bases which can be used in the reaction include metal hydroxides, such as sodium hydroxide, potassium hydroxide, and calcium hydroxide; and metal hydrides, such as sodium hydride, potassium hydride, and calcium hydride.

Where a metal hydroxide is used as a base, an organic solvent which increases solubility of the reactant reagents and is easily miscible with water and stable to an alkali is used. Such solvents preferably include ethers, e.g., tetrahydrofuran (hereinafter abbreviated as THF), dioxane, and diglyme. A water-immiscible organic solvent may also be used if stable to an alkali. Such solvents include aromatic hydrocarbons, e.g., toluene, xylene, and benzene. In the latter cases, it is preferable to use a phase transfer catalyst, preferably a tetrabutylammonium salt. Where a metal hydride is used as a base, it is preferable to use the above-mentioned solvents after drying. That is, an ether, such as THF, dioxane or diglyme, or an aromatic hydrocarbon, such as toluene, xylene or benzene but preferably THF, is used, after drying.

While the reaction temperature and time may be selected appropriately, it is recommended to carry out the reaction at room temperature or lower in order to prevent the acrylamide compound (III) from polymerizing.

The resultant compound, as represented by formula (IV) shown below, is a novel compound which is useful as an intermediate for synthesizing various 22-oxa-cholecalciferol derivatives.

The intermediate product represented by formula (IV):

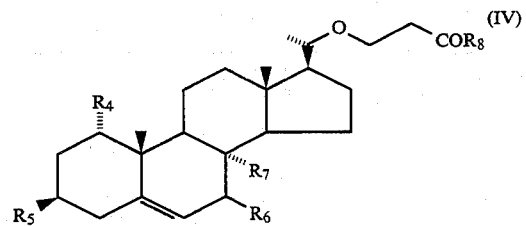

wherein $R_4$, $R_5$, $R_6$, $R_7$, and $R_8$ are as defined above, is then reacted with a compound represented by formula (V):

$$R_9X \quad (V)$$

wherein $R_9$ represents a lower alkyl group having from 1 to 5 carbon atoms; and X represents an alkali metal, an alkaline earth metal halide or a cerium halide, to obtain a compound represented by formula (VI):

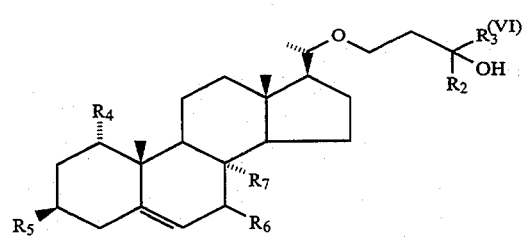

wherein $R_2$ and $R_3$, which may be the same or different, each represent a lower alkyl group having from 1 to 5 carbon atoms; and $R_4$, $R_5$, $R_6$, and $R_7$ are as defined above.

Typical examples of the compound of formula (V) are methyl lithium, butyl lithium, methylmagnesium bromide, ethylmagnesium bromide, and methylcerium chloride.

An aprotic solvent in which the organometallic compound does not decompose and by-production can be controlled is suitably used. Examples of preferred solvents are ethers, such as THF and dimethyl ether. These solvents are used in a dehydrated state in a known manner. While the reaction temperature and time may be selected appropriately, it is recommended to carry out the reaction at a temperature of from $-30°$ up to room temperature for a period of from several tens of minutes to several hours so as to prevent the compound (IV) as much as possible from returning to the former compound (II) due to elimination reaction.

Where $R_6$ and $R_7$ in the resulting compound (IV) each represent a hydrogen atom, the compound must be converted to a compound wherein $R_6$ and $R_7$ are taken together to form a double bond, i.e., a 5,7-diene compound, before it is led to a vitamin D skeleton. This can easily be achieved in a usual manner, for example, by the process described in Japanese Patent Public Disclosure No. 71055/78 as shown by the following reaction scheme (2):

[Reaction Scheme (2)]

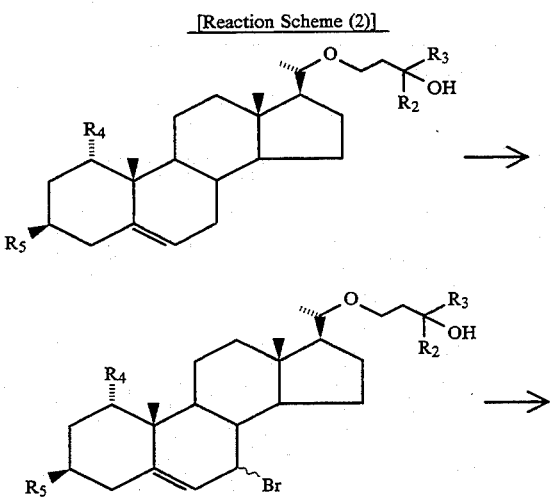

-continued
[Reaction Scheme (2)]

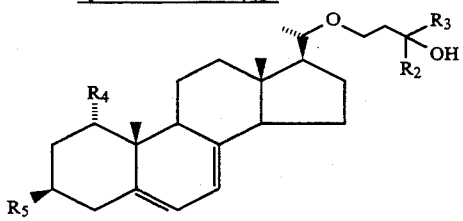

wherein $R_2$, $R_3$, $R_4$, and $R_5$ are as defined above.

That is, the 7-position of the steroid skeleton is halogenated with an allyl-position halogenating reagent, and the resulting compound is then subjected to dehydrohalogenation with a base to obtain a 5,7-diene compound.

The allyl-position halogenating reagent which can be used includes N-bromosuccinimide, N-chlorosuccinimide, and 1,3-dibromo-5,5-dimethylhydantoin. Solvents inert to halogenation reaction, preferably non-polar solvents, e.g., n-hexane and carbon tetrachloride, are used. If desired, reaction may be accelerated by irradiation or by addition of a radical reaction initiator, such as azobisisobutyronitrile (hereinafter abbreviated as AIBN).

The base which can be used for the dehydrohalogenation reaction includes organic bases, such as 2,4,6-trimethylpyridine (γ-collidine), 2,6-lutidine, and pyridine type ion-exchange resins; and inorganic bases, such as lithium carbonate and potassium carbonate. While the kind of the reaction solvent, the reaction temperature, and the reaction time may be decided appropriately depending on the kind of the base used, it is recommended to carry out the reaction by heating under reflux in toluene in the presence of γ-collidine as a base for a period of about 10 minutes.

The above reaction is sometimes accompanied by by-production of a 4,6-diene compound due to double bond shift in addition to the desired 5,7-diene compound. This being the case, purification may be effected by directly subjecting the reaction mixture to column chromatography on silica gel, or by 1,4-addition of a compound represented by formula (VII):

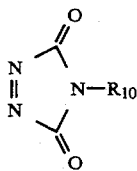

(VII)

to the 5,7-diene compound, isolating the 1,4-adduct, and subjecting the adduct to release elimination reaction to restore the 5,7-diene compound. In the above addition reaction, the 4,6-diene compound does not form an adduct.

Elimination reaction of a 1,4-adduct has conventionally been performed by using a powerful reducing agent, such as lithium aluminum hydride, or an inorganic base in a high-boiling solvent and is inapplicable to an adduct having such a functional group as cannot withstand a reduction reaction or a functional group instable to a base. Therefore, adoption of the conventional elimination reaction as a method for separation and purification as in the present invention has been limited.

In this regard, the inventors have found a technique for accomplishing the elimination reaction under a neutral condition without adversely affecting most functional groups, the technique comprising heating the 1,4-adduct in an aprotic polar solvent, such as 1,3-dimethyl-2-imidazolidinone (hereinafter abbreviated as DMI) or N,N-dimethylformamide (hereinafter abbreviated as DMF), in the absence of a catalyst to release a desired compound in high yield. While the reaction temperature and time may be selected appropriately, it is recommended for minimizing by-products and ensuring a high yield to carry out the reaction in DMI at a temperature of from 100° to 150° C. for several hours.

The compound of formula (VII) which can be used in the present invention preferably includes 4-phenyl-1,2,4-triazoline-3,5-dione.

Where $R_4$ or $R_5$ in the thus obtained compound of formula (VI) in which $R_6$ and $R_7$ are taken together to form a double bond is a protected hydroxyl group, the protecting group is removed in a usual manner to provide a compound wherein $R_4$ or $R_5$ is a hydroxyl group.

The resulting compound can easily be converted to a 22-oxacholecalciferol derivative represented by formula (I):

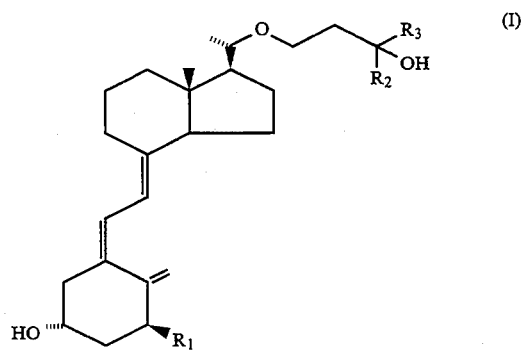

(I)

wherein $R_1$ represents a hydrogen atom or a hydroxyl group; and $R_2$ and $R_3$, which may be the same or different, each represent a lower alkyl group having from 1 to 5 carbon atoms, in a known manner, for example, in accordance with the process described in Japanese Patent Public Disclosure No. 84555/75, which consists of light irradiation in an inert solvent followed by thermal isomerization.

The compound of formula (I) wherein $R_1$ is a hydrogen atom; and $R_2$ and $R_3$ each represent a lower alkyl group, such as a methyl group, is a novel 22-oxa-cholecalcifero derivative exhibiting differentiation inducing activity and cell proliferation inhibitory activity.

The present invention will now be illustrated in greater detail with reference to Examples, but the present invention should not be construed as being limited thereto.

EXAMPLE 1

Preparation of 1α,3β-Dihydroxy-20S-(3-methyl-3-hydroxybutyloxy)-9,10-secopregna-5,7,10(19)-triene 1) Preparation of 1α,3β-Bis(t-butyldimethylsilyioxy)-20S-{2-(dimethylaminocarbonyl)ethyloxy}-5-pregnene:

In 12 l of THF was dissolved 1.95 kg of 1α,3β-bis(t-butyldimethylsilyloxy)-20S-hydroxy-5-pregnene, and the solution was cooled to 0° C. To the solution were added 1.06 kg of dimethylacrylamide and 215 g of sodium hydride, and the mixture was allowed to react at 0° C. for 8 hours. After cooling, 2.8 l of a saturated ammonium chloride aqueous solution was added dropwise to the reaction mixture, and 15 l of a saturated sodium chloride aqueous solution and 18 l of ethyl acetate were added thereto. The organic layer was washed with a saturated aqueous solution, dried over anhydrous magnesium sulfate, and concentrated to remove the solvent. To the residue was added 6 l of n-hexane, and the thus formed crystal was collected by filtration and dried to obtain 1.66 kg (73%) of the title compound.

Melting point: 148°–150° C. (as recrystallized from methanol)

IR (Kbr) cm$^{-1}$:
2956, 2860, 1652, 1254, 1068, 890, 840, 772

$^1$H-NMR (CDCl$_3$) δ:
0.03 (3H, s), 0.05 (3H, s), 0.06 (3H, s), 0.08 (3H, s), 0.64 (3H, s), 0.88 (6H, s), 0.95 (3H, s), 1.15 (3H, d, J=5.9Hz), 2.15–2.35 (2H, m), 2.56 (1H, m), 2.93 (3H, s), 3.02 (3H, s), 3.27 (1H, m), 3.57 (1H, m), 3.76 (1H, brs), 3.86 (1H, m), 3.90 (1H, m), 5.46 (1H, d, J=5.6Hz)

Elementary Analysis for C$_{38}$H$_{71}$NO$_4$Si$_2$:
Cacld. (%): C 68.93; H 10.81; N 2.12; Si 8.48
Found (%): C 68.83.; H 10.84; N 2.16; Si 8.5

2) Preparation of 1α,3β-Bis(t-butyldimethylsilyloxy)-20S-(3-methyl-3-hydroxybutyloxy)-5-pregnene:

Cerium (III) chloride heptahydrate (3.08 kg) was dehydrated in an electrical oven at 250° C. for 2 hours, and the resulting anhydrous compound was further dried in vacuo in a reaction vessel at 120° C. for 3 hours. After purging the reaction vessel with argon, 8.0 l of dried THF was added thereto, followed by stirring at room temperature for 1 hour. The mixture was cooled to −20° C., and 7.5 l of a 1 mol/l THF solution of methylmagnesium bromide was added thereto, followed by allowing the mixture to react for 30 minutes. To the reaction mixture was added 1.62 kg of 1α,3β-bis(t-butyldimethylsilyloxy)-20S-{2-(dimethylaminocarbonyl)ethyloxy}-5-pregnene, and the mixture was reacted at that temperature for 30 minutes. The reaction mixture was added dropwise to 20 l of water having dissolved therein 1.0 kg of ammonium chloride. The organic layer was separated, and the aqueous layer was re-extracted with 10 l of ethyl acetate. The organic layers were combined and dried over anhydrous magnesium sulfate, followed by concentration to remove the solvent to give 1α,3β-bis(t-butyldimethylsilyloxy)-20S-(3-oxobutyloxy)-5-pregnene.

Melting point: 105°–106° C. (as recrystallized from methanol)

IR (KBr) cm$^{-1}$:
2936, 1728, 1464, 1378, 1258, 1096, 886, 872, 838, 774

$^1$H-NMR (CDCl$_3$) δ:
0.03 (3H, s), 0.04 (3H, s), 0.06 (3H, s), 0.0S (3H, s), 0.80 (3H, s), 0.87 (18H, s), 0.99 (3H, s), 1.14 (3H, d, J=5.6Hz), 2.15–2.28 (5H, m), 2.61 (2H, m), 3.23 (1H, m), 3.52 (1H, m), 3.77 (1H, brs), 3.80 (1H, m), 3.98 (1H, m), 5.44 (1H, d, J=5.6Hz)

Elementary Analysis for C$_{37}$H$_{68}$O$_4$Si$_2$:
Calcd. (%): C 70.19; H 10.83; Si 8.87
Found (%): C 70.05; H 10.81; Si 8.9

The product was again subjected to the above-mentioned reaction to obtain a crude title compound. The crude product was suspended in methanol, and the precipitated crystal was collected by filtration and dried to afford 1.12 kg (73%) of the title compound.

Melting Point: 168°–169° C. (as recrystallized from methanol)

IR (KBr) cm$^{-1}$:
3540, 2960, 1464, 1382, 1258, 1150, 1090, 972, 886, 872, 838, 812, 774

$^1$H-NMR (CDCl$_3$) δ:
0.03 (3H, s), 0.05 (3H, s), 0.06 (3H, s), 0.08 (3H, s), 0.66 (3H, s), 0.88 (18H, s), 0.95 (3H, s), 1.18 (3H, s), 2.20–2.28 (2H, m), 3.25 (1H, m), 8.47 (1H, m), 3.76 (1H, brs), 3.81 (1H, m), 4.85 (1H, m), 5.45 (1H, d, J=5.6Hz)

Elementary Analysis for C$_{38}$H$_{72}$O$_4$Si$_2$:
Calcd. (%): C 70.31; H 11.18; Si 8.65
Found (%): C 70.41; H 11.10; Si 8.7

3) Preparation of 1α,3β-Bis(t-butyldimethylsilyloxy)-20S-(3-methyl-3-hydroxybutyloxy)-5,7-pregnadiene:

In 300 ml of n-hexane was dissolved 32.5 g of 1α,3β-bis(t-butyldimethylsilyloxy)-20S-(3-methyl-3-hydroxybutyloxy)-5-pregnene, and 11.1 g of N-bromosuccinimide (hereinafter abbreviated as NBS) and 2.46 g of AIBN were added thereto, followed by heating under reflux for 30 minutes. After cooling, any insoluble matter was removed by filtration, and the mother liquor was concentrated. The residue was dissolved in 200 ml of toluene, and 25 ml of γ-collidine was added to the solution, followed by heat-refluxing for 1 hour. After cooling, any insoluble matter was removed by filtration, and to the filtrate was added 200 ml of n-hexane. The reaction mixture was washed successively with 300 ml of 1N hydrochloric acid, 200 ml of a saturated sodium hydrogencarbonate aqueous solution, and 200 ml of a saturated sodium chloride aqueous solution. The organic layer was dried over anhydrous magnesium sulfate, followed by concentration to about 100 ml. To the concentrate was added 500 ml of acetonitrile, and the mixture was stirred under cooling with ice for 1 hour. The thus precipitated crystal was collected by filtration, the resulting crude crystal was dissolved in 100 ml of ethyl acetate, and the solution was added to 500 ml of acetonitrile. The mixture was stirred while cooling with ice for 1 hour, and the crystal formed was collected by filtration and dried to obtain 12.8 g (40%) of the title compound.

Purification by 1,4-Addition:

The mother liquor left after collection of the above crude crystal and that after collection of the purified crystal were combined and concentrated. The concentrate was dissolved in 200 ml of methylene chloride, and 3.0 g of 4-phenyl-1,2,4-triazoline-3,5-dione (hereinafter abbreviated as PTAD) was added thereto, followed by stirring at room temperature for 30 minutes. The solvent was removed by evaporation, and the residue was purified by silica gel column chromatography using a 3:1 (by volume) mixture of n-hexane and ethyl acetate as an eluent to obtain 3.63 g of a PTAD 1,4-adduct as an oily substance.

IR (KBr) cm$^{-1}$:
2960, 2864, 1756, 1704, 1656, 1474, 1400, 1254, 1104, 1058, 838, 776

$^1$H-NMR (CDCl$_3$) δ:
0.03 (3H, s), 0.05 (3H, s), 0.06 (3H, s), 0.10 (3H, s), 0.70 (3H, s), 0.82 (3H, s), 1.11 (18H, s), 1.17 (3H, m), 1.29 (6H, s), 2.34 (1H, m), 2.44–2.55 (2H, m), 3.16 (1H, m), 3.28 (1H, m), 3.40 (1H, m), 3.53–3.74 (2H, m), 4.67 (1H, m), 6.10 (1H, d, J=8.3Hz), 6.26 (1H, d, J=8.3Hz), 7.15–7.37 (5H, m)

Elementary Analysis for C$_{46}$H$_{75}$N$_3$O$_6$Si$_2$:
Calcd. (%): C 67.19; H 9.91; N 5.11.

Found (%): C 66.8S; H 8.97; N 5.06

The resultant 1,4-adduct was dissolved in 36 ml of DMI, and the solution was heated at 140° C. for 2 hours. After cooling, 40 ml of n-hexane was added thereto, and the mixture was washed three times with a saturated sodium chloride aqueous solution and dried over anhydrous magnesium sulfate. The solvent was distilled away, and the residue was crystallized from 20 ml of methanol to obtain 1.7 g (5.3%) of the title compound, giving the total yield of 14.5 g (45.3%).

Melting Point: 150°–151° C. (recrystallized from acetonitrile)

IR (KBr) cm$^{-1}$:
3540, 2964, 2864, 1464, 1382, 1258, 1150, 1100, 1084, 970, 880, 838, 774

$^1$H-NMR (CDCl$_3$) δ:
0.05 (3H, s), 0.06 (6H, s), 0.10 (3H, s), 0.60 (3H, s), 0.87 (18H, s), 0.89 (3H, s), 1.20 (3H, d, J=3.2Hz), 1.22 (3H, s), 1.23 (3H, s), 2.30–2.36 (2H, m), 2.78 (1H, m), 3.26 (1H, m), 3.49 (1H, m), 3.69 (1H, brs), 3.84 (1H, m), 4.04 (1H, m), 5.32 (1H, d, J=5.6Hz), 5.58 (1H, m)

Elementary Analysis for C$_{38}$H$_{70}$O$_4$Si$_2$:
Calcd. (%): C 70.53; H 10.90
Found (%): C 70.16; H 10.83

4) Preparation of 1α,3β-Dihydroxy-20S-(3-methyl-3-hydroxybutyloxy)-5,7-pregnadiene:

In 70 ml of THF was dissolved 14.3 g of 1α,3β-bis(t-butyldimethylsilyloxy)-20S-(3-methyl-3-hydroxybutyloxy)-5,7-pregnadiene, and 133 ml of a 1 mol/l THF solution of tetra-n-butylammonium chloride (hereinafter abbreviated as TBAF) was added thereto, followed by heating under reflux for 2 hours. To the reaction mixture was added 100 ml of ethyl acetate, and the mixture was washed successively with 0.5N hydrochloric acid, a saturated sodium hydrogencarbonate aqueous solution, and a saturated sodium chloride aqueous solution and dried over anhydrous magnesium sulfate. The solvent was removed by distillation. Crystallization of the residue from acetone furnished 8.59 g (93%) of the title compound.

Melting Point: 181°–183° C. (recrystallized from acetonitrile)

IR (KBr) cm$^{-1}$:
3388, 2972, 2880, 1464, 1378, 1224, 1154, 1084, 1050

$^1$H-NMR (CDCl$_3$) δ:
0.61 (3H, s), 0.91 (3H, s), 1.20 (3H, d, J=6.3Hz), 1.23 (3H, s), 1.26 (3H, s), 2.13 (1H, m), 2.34 (1H, m), 2.54 (1H, m), 2.73 (1H, m), 3.27 (1H, m), 3.49 (1H, m), 3.76 (1H, brs), 3.85 (1H, m), 4.05 (1H, m), 5.38 (1H, dd, J=2.6, 5.5Hz), 5.71 (1H, dd, J=1.6, 5.3Hz)

Elementary Analysis for C$_{26}$H$_{42}$O$_4$:
Calcd. (%): C 74.60; H 10.11
Found (%): C 74.36; H 9.93

5) Preparation of 1α,3β-Dihydroxy-20S-(3-methyl-3-hydroxybutyloxy)-9,10-secopregna-5-(10),6,8-triene:

In 220 ml of THF was dissolved 12.6 g of 1α,3β-dihydroxy-20S-(3-methyl-3-hydroxybutyloxy)-5,7-pregnadiene, and the solution was irradiated with light from a high-pressure mercury lamp via a Vycol filter for 225 minutes. The reaction mixture was concentrated, and the residue was crystallized from 90 ml of acetone to recover 5.57 g of the starting compound (recovery: 44%). The mother liquor was purified by fractional high performance liquid chromatography (SYSTEM-500 produced by Waters Co.; eluent: ethyl acetate:methylene chloride=5:2 by volume) to obtain 3.64 g (29%) of the crude title compound.

Melting Point: 81°–94° C. (recrystallized from ethyl acetate)

IR (KBr) cm$^{-1}$:
3340, 1680, 1150, 1040

$^1$H-NMR (CDCl$_3$) δ:
0.67 (3H, s), 1.21 (3H, d, J=5.9Hz), 1.25 (3H, s), 1.26 (3H, s), 1.2–1.6 (4H, m), 1.61–1.90 (8H, m), 1.90–2.23 (7H, m), 2.46 (1H, dd, J=2.6, 14.5Hz), 3.28 (1H, m), 3.49 (1H, m), 3.88 (1H, m), 4.03 (1H, m), 4.20 (1H, brs), 5.51 (1H, brs), 5.75 (1H, d, J=12.2Hz), 5.82 (1H, d, J=12.2Hz)

UV (EtOH) λ$_{max}$: 260 nm (ε9300)

6) Preparation of 1α,3β-Dihydroxy-20S-(3-methyl-3-hydroxybutyloxy)-9,10-secopregna-5,7,10(19)-triene:

In 70 ml of THF was dissolved 3.64 g of crude 1α,3β-dihydroxy-20S-(3-methyl-3-hydroxybutyloxy)-9,10-secopregna-5(10),6,8-triene, and the solution was allowed to stand at room temperature for 4 days. The solvent was removed by evaporation, and the residue was purified by fractional high performance liquid chromatography (SYSTEM-500 produced by Waters Co.; eluent: ethyl acetate:methylene chloride=5:4 by volume) to obtain 1.40 g of the title compound as an oily substance. Crystallization from ethyl acetate and n-hexane gave 1.08 g of the title compound in a yield of 8.6% based on the 1α,3β-dihydroxy-20S-(3-methyl-3-hydroxybutyloxy)-5,7-pregnadiene.

Melting Point:
112°–115° C. (crystallized from a mixed solvent of ethyl acetate and n-hexane)

IR (KBr) cm$^{-1}$:
3400, 1645, 1160, 1020

$^1$H-NMR (CDCl$_3$) δ:
0.53 (3H, s), 1.18–1.32 (10H, m), 1.46–1.62 (4H, m), 1.63–1.75 (4H, m), 1.82–2.20 (8H, m), 2.30 (1H, dd, J=7.3, 13.2Hz), 2.58 (1H, dd, J=3.6, 7.0Hz), 2.82 (1H, dd, J=0.3, 12.9Hz), 3.26 (1H, m), 3.47 (1H, m), 3.85 (1H, m), 4.22 (1H, m), 4.42 (1H, m), 4.98 (1H, s), 5.32 (1H, s), 6.02 (1H, d, J=11.2Hz), 6.35 (1H, d, J=11.2Hz)

UV (EtOH) λ$_{max}$: 264 nm (ε17000)

EXAMPLE 2

Preparation of 1α,3β-Bis(t-butyldimethylsilyloxy)-20S-(3-methyl-3-hydroxybutyloxy)-5,7-pregnadiene 1) Preparation of 1α,3β-Bis(t-butyldimethylsilyloxy)-20S-{2-(dimethylaminocarbonyl)ethyloxy}-5,7-pregnadiene:

In 1.2 l of THF was dissolved 825 g of 1α,3β-bis(t-butyldimethylsilyloxy)-20S-hydroxy-5,7-pregnadiene, and the solution was cooled to 0° C. To the solution were added 688 g of dimethylacrylamide and 175 g of sodium hydride, and the mixture was allowed to react at 0° C. for 8 hours. To the reaction mixture was added dropwise 700 ml of a saturated ammonium chloride aqueous solution while cooling, and 4 l of a saturated sodium chloride aqueous solution and 5 l of ethyl acetate were further added thereto. The organic layer was washed with a saturated aqueous solution and dried over anhydrous magnesium sulfate. The solvent was removed by evaporation, and the residue was purified by silica gel column chromatography using a 3:1 (by volume) mixture of n-hexane and ethyl acetate and then ethyl acetate as an eluent to obtain 822 g (85%) of the title compound.

Melting Point:
137°–139° C. (recrystallized from ethyl acetate)

$^1$H-NMR (CDCl$_3$) δ:

0.03 (3H, s), 0.04 (6H, s), 0.08 (3H, s), 0.64 (3H, s), 0.88 (6H, s), 0.95 (3H, s), 1.15 (3H, d, J=5.9Hz), 2.15-2.35 (2H, m), 2.56 (1H, m), 2.93 (3H, s), 3.02 (3H, s), 3.27 (1H, m), 3.57 (1H, m), 3.76 (1H, brs), 3.86 (1H, m), 3.90 (1H, m), 5.29 (1H, m), 5.56 (1H, m)

2) Preparation of 1α,3β-Bis(t-butyldimethylsilyloxy)-20S-(3-methyl-3-hydroxybutyloxy)-5,7-pregnadiene:

Cerium (III) chloride heptahydrate (561 g) was dehydrated in an electrical oven at 250° C. for 2 hours, and the resulting anhydrous compound was further dried in vacuo in a reaction vessel at 140° C. for 2 hours. After purging the reaction vessel with argon, 1.35 l of dried THF was added thereto, followed by stirring at room temperature for 1 hour. The mixture was cooled to −20° C., and 1.36 l of a 1 mol/l THF solution of methylmagnesium bromide was added thereto, followed by allowing the mixture to react for 30 minutes. To the reaction mixture was added 300 g of 1α,3β-bis(t-butyldimethylsilyloxy)-20S-{2-(dimethylaminocarbonyl)ethyloxy}-5,7-pregnene, and the mixture was reacted at that temperature for 30 minutes. The reaction mixture was added dropwise to 4 l of water having dissolved therein 200 g of ammonium chloride. The organic layer was separated, and the aqueous layer was re-extracted with 5 l of ethyl acetate. The organic layers were combined and dried over anhydrous magnesium sulfate. Evaporation of the solvent gave 1α,3β-bis(t-butyldimethylsilyloxy)-20S-(3-oxobutyloxy)-5,7-pregnadiene. The resulting compound was again subjected to the above-mentioned reaction. The crude product was suspended in methanol, and the crystal thus formed was collected by filtration and dried to obtain 229 g (80%) of the title compound.

Melting point:
150°-151° C. (as recrystallized from acetonitrile)
IR (KBr) cm$^{-1}$:
3540, 2964, 2864, 1464, 1382, 1258, 1150, 1100, 1084, 970, 880, 838, 774
$^1$H-NMR (CDCl$_3$) δ:
0.04 (3H, s), 0.05 (6H, s), 0.09 (3H, s), 0.60 (3H, s), 0.87 (18H, s), 0.89 (3H, s), 1.20 (3H, d, J=5.9Hz), 1.22 (3H, s), 1.23 (3H, s), 2.30-2.36 (2H, m), 2.78 (1H, m), 3.26 (1H, m), 3.49 (1H, m), 3.69 (1H, brs), 3.84 (1H, m), 4.04 (1H, m), 5.32 (1H, d, J=2.6Hz), 5.58 (1H, d, J=5.6Hz)

EXAMPLE 3

1) Preparation of 3β-(t-Butyldimethylsilyloxy)-5-androsten-17-one:

In 300 ml of DMF was dissolved 56.7 g of dehydroepiandrosterone, and 41.7 g of imidazole and 46.08 g of t-butyldimethylchlorosilane were added to the solution, followed by stirring at room temperature for 2 hours. After completion of the reaction. 150 ml of methanol was added to the reaction mixture. The thus formed crystal was collected by filtration, washed with 100 ml of methanol, and dried to obtain 73.7 g (93.1%) of the title compound.

Melting Point: 149° C. (recrystallized from methanol)
IR (Kbr) cm$^{-1}$:
2932, 1748, 1094, 774
$^1$H-NMR (CDCl$_3$) δ:
0.05 (6H, s), 3.42-3.54 (1H, m), 5.34 (1H, d, J=5.0Hz)
Elementary Analysis for C$_{25}$H$_{42}$O$_2$Si:
Calcd. (%): C 74.57; H 10.51; Si 6.97
Found (%): C 74.52; H 10.35; Si 6.9

2) Preparation of 3β-(t-Butyldimethylsilyloxy)-pregna-5,17-(20)-diene:

In 400 ml of THF was dissolved 250 g of ethyltriphenylphosphonium bromide, and 70.0 g of potassium t-butoxide was added thereto, followed by stirring at 40° C. for 1.5 hours. Subsequently, 70.0 g of 3β-(t-butyldimethylsilyloxy)-5-androsten-17-one was added thereto, and the mixture was stirred at 60° C. for 1.5 hours. After cooling, the reaction mixture was poured into a mixture of 200 ml of n-hexane and 400 ml of water. The organic layer was separated, and the aqueous layer was re-extracted with 300 ml of n-hexane. The organic layers were combined and dried over anhydrous magnesium sulfate, followed by evaporation. To the residue was added 300 ml of n-hexane, followed by stirring at room temperature for 2 hours. The precipitated crystal was collected by filtration, and the filtrate was concentrated. The residue was crystallized from a mixture of 200 ml of acetone and 300 ml of methanol to obtain 68.8 g (95.4%) of the title compound.

Melting Point: 98°-101° C. (recrystallized from methanol)
IR (Kbr) cm$^{-1}$:
2940, 2860, 1254, 1094, 888, 838, 776
$^1$H-NMR (CDCl$_3$) δ:
0.06 (6H, s), 3.42-3.54 (1H, m), 5.09-5.17 (1H, m), 5.33 (1H, d, J=5.3Hz)
Elementary Analysis for C$_{27}$H$_{46}$O$_2$Si:
Calcd. (%): C 78.19; H 11.18; Si 6.77
Found (%): C 78.29; H 11.24; Si 6.4

3) Preparation of 3β-(t-Butyldimethylsilyloxy)-20S-hydroxy-5-pregnene:

To 500 ml of a 0.5M THF solution of 9-borabicyclo[3.3.1]nonane (9-BBN) was added 65.7 g of 3β-(t-butyldimethylsilyloxy)-pregna-5,17-(20)-diene, and the mixture was stirred at 40° C. for 2 hours. The reaction mixture was cooled to 0° C., and 420 ml of a 3N sodium hydroxide aqueous solution and 340 g of a 30% hydrogen peroxide aqueous solution were added dropwise thereto, followed by vigorously stirring at room temperature for 3 hours. To the reaction mixture was added 500 ml of ethyl acetate, and the organic layer was separated. The aqueous layer was extracted twice with 150 ml portions of ethyl acetate. The organic layers were combined, washed successively with a saturated sodium hydrogencarbonate aqueous solution and a saturated sodium chloride aqueous solution, dried over anhydrous magnesium sulfate, and evaporated to remove the solvent. The residue was crystallized from 250 ml of methanol, and the resulting crystal was collected by filtration and dried to obtain 56.3 g (82%) of the title compound.

Melting Point: 162°-163° C. (recrystallized from methanol)
IR (Kbr) cm$^{-1}$:
3392, 2940, 1462, 1386, 1258, 1088, 888, 870, 840, 772
$^1$H-NMR (CDCl$_3$) δ:
0.05 (3H, s), 0.06 (3H, s), 3.46-3.50 (1H, m), 3.68-3.73 (1H, m), 5.31 (1H, d, J=4.9Hz)
Elementary Analysis for C$_{27}$H$_{48}$O$_2$Si:
Calcd. (%): C 74.94; H 11.18; Si 6.49
Found (%): C 74.31; H 11.33; Si 6.4

4) Preparation of 3β-(t-Butyldimethylsilyloxy)-20S-{2-(dimethylaminocarbonyl)ethyloxy}-5-pregnene:

In 420 ml of THF was dissolved 53.0 g of 3β-(t-butyldimethylsilyloxy)-20S-hydroxy-5-pregnene, and the solution was cooled to 0° C. To the solution were added 48.6 g of dimethylacrylamide and 9.8 g of sodium hydride, and the mixture was allowed to react at 0° C. for 8 hours. To the reaction mixture was added dropwise 100 ml of a saturated ammonium chloride aqueous solution while cooling, and 400 ml of ethyl acetate was further added thereto. The organic layer was washed with a saturated aqueous solution, dried over anhydrous magnesium sulfate, and evaporated to remove the solvent. The residue was crystallized from 200 ml of n-hexane, and the thus formed crystal was collected by filtration and dried to obtain 26.4 g of the title compound. The filtrate was concentrated, and the residue was purified by silica gel column chromatography to recover 29.2 g of the title compound, giving the total yield of 55.6 g (73%).

Melting Point: 142° C. (recrystallized from methanol)
IR (KBr) cm$^{-1}$:
2940, 1632, 1258, 1088, 890, 872, 840, 772
$^1$H-NMR (CDCl$_3$) δ:
0.04 (3H, s), 0.05 (3H, s), 2.93 (3H, s), 3.02 (3H, s), 5.30 (1H, d, J=5.0Hz)
Elementary Analysis for C$_{32}$H$_{57}$NO$_3$Si:
Calcd. (%): C 72.26; H 10.80; N 2.63; Si 5.28
Found (%): C 72.12; H 10.67; N 2.66; Si 5.2

5) Preparation of 3β-(t-Butyldimethylsilyloxy)-20S-(3-methyl-3-hydroxybutyloxy)-5-pregnene:

Dehydrated cerium (III) chloride (109 g) was further dried in vacuo in a reaction vessel at 140° C. for 2 hours. After purging the reaction vessel with argon, 320 ml of dried THF was added thereto, followed by stirring at room temperature for 1 hour. The mixture was cooled to −10° C., and 400 ml of a 1 mol/l THF solution of methylmagnesium bromide was added thereto, followed by allowing the mixture to react for 30 minutes. To the reaction mixture was added 35.2 g of 3β-(t-butyldimethylsilyloxy)-20S-{2-(dimethylaminocarbonyl)ethyloxy}-5-pregnene, and the mixture was reacted at that temperature for 30 minutes. The reaction mixture was added dropwise to a 1N ammonium chloride aqueous solution. The organic layer was separated, and the aqueous layer was re-extracted with 200 ml of ethyl acetate. The organic layers were combined and dried over anhydrous magnesium sulfate. Evaporation of the solvent gave 3β-bis(t-butyldimethylsilyloxy)-20S-(3-oxobutyloxy)-5-pregnene.

Melting point:
109°–110° C. (as recrystallized from methanol)
IR (Kbr) cm$^{-1}$:
2940, 2900, 1718, 1372, 1258, 1088, 888, 872, 840, 772
$^1$H-NMR (CDCl$_3$) δ:
0.05 (6H, s), 2.18 (3H, s), 3.21–3.26 (1H, m), 5.30 (1H, d, J=5.0Hz)
Elementary Analysis for C$_{31}$H$_{54}$O$_3$Si:
Calcd. (%): C 74.05; H 10.82; Si 5.59
Found (%): C 74.09; H 10.96; Si 5.6

The product was again subjected to the above-mentioned reaction to obtain the crude title compound, which was suspended in methanol. The crystal thus formed was collected by filtration and dried to obtain 45.0 g (87%) of the title compound.

Melting Point: 168° C. (recrystallized from methanol)
IR (Kbr) cm$^{-1}$:
3520, 2939, 1382, 1256, 1096, 886, 838, 778
$^1$H-NMR (CDCl$_3$) δ:
0.04 (3H, s), 0.05 (3H, s), 1.17 (3H, d, J=5.9Hz), 1.22 (6H, s), 5.31 (1H, d, J=5.0Hz)
Elementary Analysis for C$_{32}$H$_{58}$O$_3$Si:
Calcd. (%): C 74.07; H 11.27; Si 5.41
Found (%): C 73.93; H 11.24; Si 5.4

6) Preparation of 3β-(t-Butyldimethylsilyloxy)-20S-(3-methyl-3-hydroxybutyloxy)-5,7-pregnadiene:

In 300 ml of n-hexane was dissolved 25.9 g of 3β-(t-butyldimethylsilyloxy)-20S-(3-methyl-3-hydroxybutyloxy)-5-pregnene, and 11.1 g of NBS and 2.46 g of AIBN were added thereto, followed by heating under reflux for 30 minutes. After cooling, any insoluble matter was removed by filtration, and the mother liquor was concentrated. The residue was dissolved in 200 ml of toluene, and 25 ml of γ-collidine was added to the solution, followed by heat-refluxing for 1 hour. After cooling, any insoluble matter was removed by filtration, and to the filtrate was added 200 ml of n-hexane. The reaction mixture was washed successively with 180 ml of 1N hydrochloric acid, 50 ml of a saturated sodium hydrogencarbonate aqueous solution, and 50 ml of a saturated sodium chloride aqueous solution. The organic layer was dried over anhydrous magnesium sulfate, followed by concentration to about 100 ml. The concentrate was added to 400 ml of acetonitrile, and the mixture was stirred under cooling with ice for 15 minutes. The thus precipitated crystal was collected by filtration, the resulting crude crystal was dissolved in 30 ml of methylene chloride, and the solution was added to 300 ml of acetonitrile. The mixture was stirred while cooling with ice for 15 minutes, and the crystal formed was collected by filtration and dried to obtain 5.52 g (21%) of the title compound.

Purification by 1,4-Addition:

The mother liquor left after collection of the above crude crystal and that after collection of the purified crystal were combined and concentrated. The concentrate was subjected to silica gel column chromatography using a 10:1 (by volume) mixture of n-hexane and ethyl acetate as an eluent. The fractions containing the title compound were collected and dissolved in 200 ml of methylene chloride. To the solution was added 6.0 g of PTAD, followed by stirring at room temperature for 45 minutes. The solvent was removed by evaporation, and the residue was purified by silica gel column chromatography using, as an eluent, a 10:1 (by volume) mixture of n-hexane and ethyl acetate and then a 2:1 (by volume) mixture of the same solvents to obtain 4.71 g of a PTAD 1,4-adduct.

Melting Point: 196°–197° C. (recrystallized from acetonitrile)
IR (Kbr) cm$^{-1}$:
3460, 2936, 1760, 1706, 1408, 1088, 862
$^1$H-NMR (CDCl$_3$) δ:
0.08 (6H, s), 1.19 (3H, d, J=5.9Hz), 1.22 (6H, s), 6.19 (1H, d, J=8.3Hz), 6.35 (1H, d, J=S.3Hz), 7.28–7.46 (5H, m)
Elementary Analysis for C$_{40}$H$_{61}$N$_3$O$_5$Si:
Calcd. (%): C 69.43; H 8.88; N 6.07; Si 4.06
Found (%): C 69.70; H 8.55; N 6.07; Si 4.0

The resultant 1,4-adduct was dissolved in 50 ml of DMI, and the solution was heated at 160° C. for 2 hours. After cooling, 40 ml of toluene was added thereto, and the mixture was washed with 50 ml of a saturated sodium chloride aqueous solution and dried over anhydrous magnesium sulfate. The solvent was distilled away, and the residue was crystallized from 50 ml of acetonitrile to obtain 2.47 g (9%) of the title compound, giving the total yield of 7.99 g (30%).

Melting Point: 147°–149° C. (recrystallized from acetonitrile)
IR (Kbr) cm$^{-1}$:

3520, 2964, 2936, 2864, 1464, 1380, 1252, 1166, 1152, 1098, 880, 838, 778

$^1$H-NMR (CDCl$_3$) δ:

0.06 (6H, s), 0.60 (3H, s), 0.88 (9H, s), 0.89 (3H, s), 1.20 (3H, d, J=6.3Hz), 1.23 (3H, s), 1.24 (3H, s), 5.38-5.41 (1H, m), 5.54 (1H, d, J=5.6Hz)

Elementary Analysis for C$_{32}$H$_{56}$O$_3$Si:

Calcd. (%): C 74.36; H 10.92; Si 5.43

Found (%): C 74.12; H 11.13; Si 5.4

7) Preparation of 3β-Hydroxy-20S-(3-methyl-3-hydroxybutyloxy)-5,7-pregnadiene:

In 40 ml of THF was dissolved 7.60 g of 3β-(t-butyldimethylsilyloxy)-20S-(3-methyl-3-hydroxybutyloxy)-5,7-pregnadiene, and 45 ml of a 1 mol/l THF solution of TBAF was added thereto, followed by stirring at room temperature for 10 hours. To the reaction mixture was added 50 ml of ethyl acetate, and the mixture was washed successively with 90 ml of 1N hydrochloric acid, 100 ml of a saturated sodium hydrogencarbonate aqueous solution, and 100 ml of a saturated sodium chloride aqueous solution and dried over anhydrous magnesium sulfate. The solvent was removed by distillation. Crystallization of the residue from 50 ml of acetone furnished 4.50 g (79%) of the title compound.

Melting Point: 162°-164° C. (recrystallized from acetonitrile)

IR (Kbr) cm$^{-1}$:

3504, 3432, 2968, 2936, 2872. 1368, 1156, 1092, 1072, 1044

$^1$H-NMR (CDCl$_3$) δ:

0.59 (3H, s), 0.91 (3H, s), 1.19 (3H, d, J=5.9Hz), 1.22 (3H, s), 1.23 (3H, s), 5.35-5.39 (1H, m), 5.55 (1H, dd, J=2.3, 5.5Hz)

Elementary Analysis for C$_{26}$H$_{42}$O$_3$:

Calcd. (%): C 77.56; H 10.51

Found (%): C 77.60; H 10.52

8) Preparation of 3β-Hydroxy-20S-(3-methyl-3-hydroxybutyloxy)-9,10-secopregna-5,7,10(19)-triene:

In 230 ml of THF was dissolved 2.30 g of 3β-hydroxy-20S-(3-methyl-3-hydroxybutyloxy)-5,7-pregnadiene, and the solution was irradiated with light from a high-pressure mercury lamp via a Vycol filter for 55 minutes. The reaction mixture was concentrated, and the residue was crystallized from 23 ml of acetone to recover 0.90 g of the starting compound (recovery: 39%). The mother liquor was purified by fractional high performance liquid chromatography (HLC-837 produced by Tosoh Corporation; eluent: ethyl acetate:-methylene chloride=1:5 by volume) to obtain 0.33 g (14%) of crude 3β-hydroxy-20S-(3-methyl-3-hydroxybutyloxy)-9,10-secopregna-5(10),6,8-triene.

$^1$H-NMR (CDCl$_3$) δ:

0.68 (3H, s), 1.20 (3H, d, J=5.9Hz), 1.22 (3H, s), 1.23 (3H, s), 1.24 (3H, s), 1.62 (3H, s), 2.35 (1H, m), 3.28 (1H, m), 3.47 (1H, m), 5.49 (1H, d, J=2.3Hz), 5.67 (1H, d, J=11.8Hz), 5.94 (1H, d, J=12.5Hz)

In 15 ml of THF was dissolved 0.33 g of the crude 3β-hydroxy-20S-(3-methyl-3-hydroxybutyloxy)-9,10-secopregna-5(10),6,8-triene, and the solution was refluxed for 2 hours. The solvent was removed by evaporation, and the residue was purified by fractional high performance liquid chromatography (HLC-837 produced by Tosoh Corporation; solvent: ethyl acetate:-methylene chloride=1:5 by volume) to obtain 0.06 g of the title compound as an oily substance in a yield of 3% based on the 3β-hydroxy-20S-(3-methyl-3-hydroxybutyloxy)-5,7-pregnadiene.

IR (Kbr) cm$^{-1}$:

3409, 2967, 2933, 2873, 1440, 1376, 1371, 1265, 1151, 1089, 1052, 738

$^1$H-NMR (CDCl$_3$) δ:

0.52 (3H, s), 1.18 (3H, d, J=6.3Hz), 1.22 (6H, s), 3.22-3.27 (1H, m), 3.79-3.87 (1H, m), 3.90-3.96 (1H, m), 4.80 (1H, d, J=1.3Hz), 5.04 (1H, d, J.=1.3Hz), 6.03 (1H, d, J=11.2Hz), 6.21 (1H, d, J=11.2Hz)

UV (EtOH) λ$_{max}$: 270 nm (ε13600)

MS m/z: 402 (M+)

What is claimed is:

1. A process for preparing a 22-oxacholecalciferol derivative represented by formula (I):

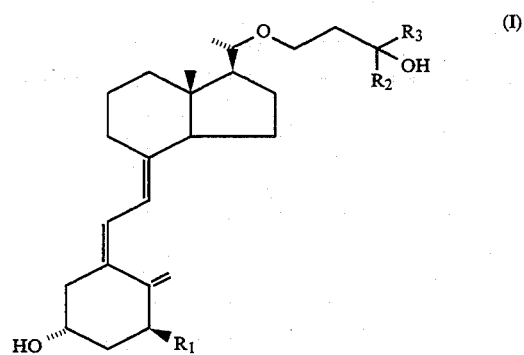

wherein R$_1$ represents a hydrogen atom or a hydroxyl group; and R$_2$ and R$_3$, which may be the same or different, each represent a lower alkyl group having from 1 to 5 carbon atoms, comprising reacting a compound represented by the formula (II):

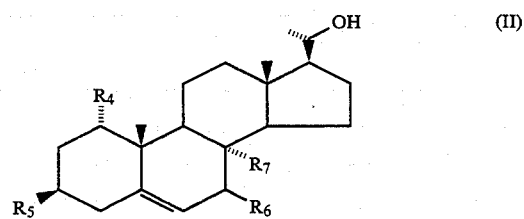

wherein R$_4$ represents a hydrogen atom, a hydroxyl group or a protected hydroxyl group; R$_5$ represents a hydroxyl group or a protected hydroxyl group; and R$_6$ and R$_7$ represent a hydrogen atom respectively or they are taken together to form a double bond, with a compound represented by formula (III):

$$CH_2=CH-COR_8 \qquad (III)$$

wherein R$_8$ represents a dialkylamino group having from 2 to 5 carbon atoms, in an organic solvent or a water/organic solvent two layer system to prepare a compound represented by formula (IV):

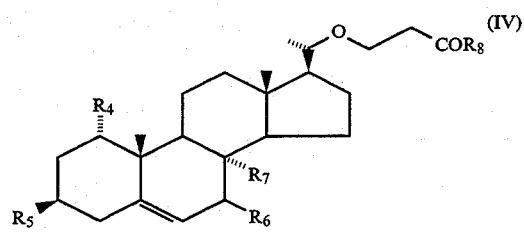

wherein $R_4$, $R_5$, $R_6$, $R_7$, and $R_8$ are as defined above, reacting the compound of formula (IV) with an organometallic compound represented by formula (V):

$$R_9X \qquad (V)$$

wherein $R_9$ represents a lower alkyl group having from 1 to 5 carbons atoms; and X represents an alkali metal, an alkaline earth metal halide or a cerium halide, to obtain a compound represented by formula (VI):

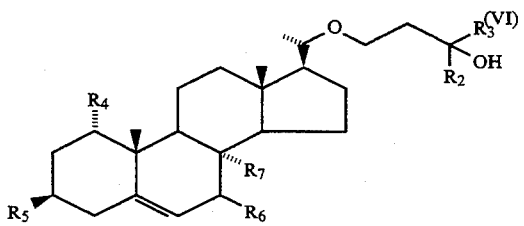

wherein $R_2$, $R_3$, $R_4$, $R_5$, $R_6$, and $R_7$ are as defined above,
when $R_6$ and $R_7$ are both H, converting said compound of formula (VI) to another compound of formula (VI) wherein $R_6$ and $R_7$ form a double bond,
irradiating with ultraviolet light the compound of formula (VI) wherein $R_6$ and $R_7$ taken together form a double bond therebetween, and
then subjecting the resulting compound to thermal isomerization in an organic solvent thereby obtaining the compound of formula (I).

2. A process as claimed in claim 1, wherein said reaction of the compound of formula (VI) wherein $R_6$ and $R_7$ represent a hydrogen atom respectively to the compound of formula (VI) wherein $R_6$ and $R_7$ are taken together to form a double bond consists of halogenation of $R_6$ and dehydrohalogenation in the presence of a basic catalyst.

3. A process as claimed in claim 1, wherein the compound of formula (III) is an acrylamide compound.

4. A process as claimed in claim 1, wherein said reacting of the compound of formula (II) and the compound of formula (III) is in the presence of a basic catalyst.

5. A process for eliminating protection in a method comprising converting a compound represented by the formula (VIII):

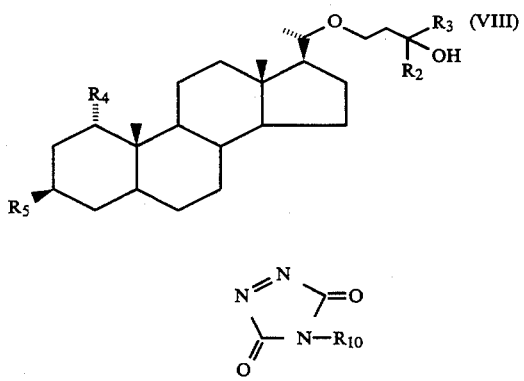

wherein $R_2$ and $R_3$, which may be the same or different, each represent a lower alkyl group having from 1 to 5 carbon atoms; $R_4$ represents a hydrogen atom, a hydroxyl group or a protected hydroxyl group; $R_5$ represents a hydroxyl group or a protected hydroxyl group; and $R_{10}$ represents a hydrogen atom, a lower alkyl group having 1 to 5 carbon atoms or a substituted or unsubstituted aryl group, to a compound represented by formula (VI):

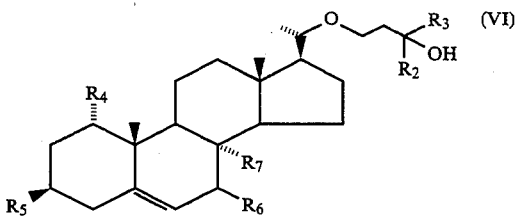

wherein $R_2$, $R_3$, $R_4$ and $R_5$ are as defined above; $R_6$ and $R_7$ represent a hydrogen atom respectively or they are taken together to form a double bond;
wherein said converting is carried out by heating the compound of formula (VIII) in an aprotic polar solvent in the absence of a catalyst.

6. A process as claimed in claim 5, wherein said solvent is 1,3-dimethyl-2-imidazolidinone.

7. A process for preparing a compound represented by formula (IV):

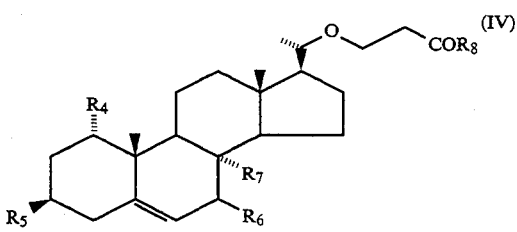

wherein $R_4$ represents a hydrogen atom, a hydroxyl group or a protected hydroxyl group; $R_5$ represents a hydroxyl group or a protected hydroxyl group; $R_6$ and $R_7$ represent a hydrogen atom respectively or they are taken together to form a double bond; and $R_8$ represents a dialkylamino group having from 2 to 5 carbon atoms, comprising reacting a compound represented by formula (II):

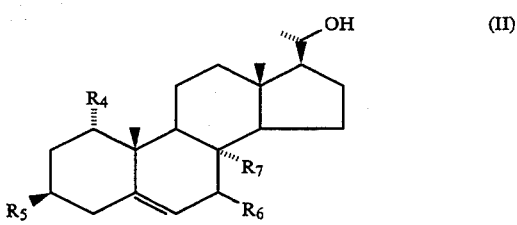

wherein $R_4$, $R_5$, $R_6$, and $R_7$ are as defined above, with a compound represented by formula (III):

$$CH_2=CH-COR_8 \qquad (III)$$

wherein $R_8$ is as defined above.

8. A compound represented by formula (IV):

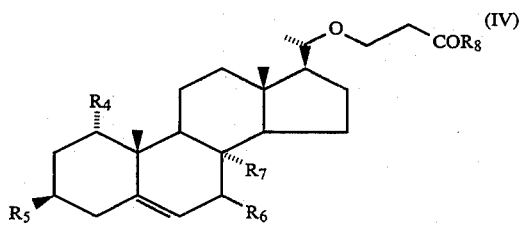 (IV)
wherein $R_4$ represents a hydrogen atom, a hydroxyl group or a protected hydroxyl group; $R_5$ represents a hydroxyl group or a protected hydroxyl group; $R_6$ and $R_7$ represent a hydrogen atom respectively or they are taken together to form a double bond; and $R_8$ represents a dialkylamino group having from 2 to 5 carbon atoms.
* * * * *

UNITED STATES PATENT AND TRADEMARK OFFICE
CERTIFICATE OF CORRECTION

PATENT NO. :    5,436,401
DATED      :    July 25, 1995
INVENTOR(S) :   M. KATO et al.

It is certified that error appears in the above-indentified patent and that said Letters Patent is hereby corrected as shown below:

Column 17, claim 5, delete the chemical formula (VIII) and insert therefor:

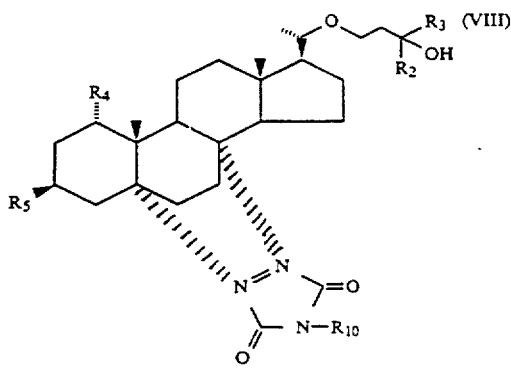

Signed and Sealed this

Twelfth Day of December, 1995

Attest:

BRUCE LEHMAN

*Attesting Officer*     *Commissioner of Patents and Trademarks*